US006620397B2

(12) United States Patent
Wettling et al.

(10) Patent No.: US 6,620,397 B2
(45) Date of Patent: Sep. 16, 2003

(54) MATERIAL AND METHOD FOR TREATING PHOTOGRAPHIC EFFLUENTS

(75) Inventors: Danielle M. Wettling, Chatenoy le Royal (FR); Olivier J. Poncelet, Chalon sur Saone (FR)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/159,680

(22) Filed: May 31, 2002

(65) Prior Publication Data

US 2003/0077547 A1 Apr. 24, 2003

(30) Foreign Application Priority Data

Jun. 11, 2001 (FR) .............................. 01 07566

(51) Int. Cl.$^7$ .............................................. C01B 33/26
(52) U.S. Cl. .................................................. 423/330.1
(58) Field of Search ...................................... 423/330.1

(56) References Cited

U.S. PATENT DOCUMENTS

| | | | | |
|---|---|---|---|---|
| 4,906,466 A | * | 3/1990 | Edwards et al. | 424/421 |
| 5,683,826 A | * | 11/1997 | Poncelet et al. | 428/702 |
| 5,882,624 A | * | 3/1999 | Kuznicki et al. | 423/700 |
| 5,888,711 A | | 3/1999 | Poncelet et al. | 430/527 |
| 5,972,831 A | * | 10/1999 | Poncelet et al. | 502/304 |

FOREIGN PATENT DOCUMENTS

EP 0937393 A1 8/1999
EP 0937682 A1 8/1999

OTHER PUBLICATIONS

Synthetic Allophane and Imogolite, Wada in J. Soil Sci. 1979, 30(2), 347–355.

Stable Hydrosols of Metallic and Bimetallic Nanoparticles Immobilized on Imogolite Fibers, L.M. Liz.–Marzan and A.P. Philipse, in J. Phys. Chem., American Chemical Society, 1995, 99, 15120–15128.

* cited by examiner

Primary Examiner—Hoa Van Le
(74) Attorney, Agent, or Firm—J. Jeffrey Hawley

(57) ABSTRACT

The present invention relates to a material and a method for treating of photographic effluents in order to eliminate microorganisms and pollutant by-products so as to control bacterial growth and thereby obtain effluents that comply with regulatory requirements. The method for preparing an oxidizing material according to the invention comprises the dispersion in colloidal form of a metal or metal compound in an aqueous solution of an inorganic aluminosilicate polymer, said aluminosilicate being able to form an inorganic gel, and said metal or metal compound being able to cause the oxidation of oxidizable products and (or) microorganisms to be eliminated, followed by the addition of a base to cause said aluminosilicate to gel. The metal is preferably silver in a powder form that is able to form a colloid when it is dispersed. The oxidizing material of the invention is efficient especially for the treatment of photographic baths, in particular wash baths placed after the fixing step.

6 Claims, 1 Drawing Sheet

MATERIAL AND METHOD FOR TREATING PHOTOGRAPHIC EFFLUENTS

FIELD OF THE INVENTION

The present invention relates to a method for preparing an oxidizing material, to the oxidizing material thus prepared, and to a method for treating effluents, and in particular to method for treating photographic effluents.

DESCRIPTION RELATIVE TO THE PRIOR ART

Many manufacturing or processing methods produce effluents that cannot be released directly into the sewers because of their composition. One example is that of the photographic industry, in which exposed films and papers pass successively through several processing steps (or "baths") that produce effluents rich in chemicals. Such processing methods for photographic films are well known (see, for example, Chimie et Physique Photographiques, Pierre Glafkides, Vol. 2, Cap. XL, pages 947–967).

Conventionally, the processing of photographic products comprises a development step and a de-silvering step. The de-silvering step comprises the bleaching of the photographic product, which consists of converting metallic silver into silver ions, followed by fixing, which consists of eliminating the silver ions contained in the photographic product. Conventionally, the photographic processing steps can also include wash and stabilizing steps.

Photographic products are generally developed automatically and as quickly as possible. During processing, the product passes through each of the steps described above. When the photographic product passes through the successive steps, non-negligible quantities of chemicals are carried over from one tank to the next, either by the photographic product itself or by the drive belts that convey the photographic product. These chemicals build up in the processing baths and thereby reduce their efficacy. The faster the photographic products are processed, the worse is the contamination of baths by the carry-over of chemicals. To counter this contamination, wash baths are intercalated between successive processing baths. In particular, after passage through a fixing or bleaching-fixing bath, the film passes through several wash baths before it enters the stabilizing bath.

The wash baths that come after the fixing step contain many substances such as sulfites, thiosulfates and (or) ammonium salts used in the fixing baths, the sulfites and thiosulfates possibly deriving also from the developer. These wash baths cannot be discarded directly into the sewers and must be treated first to eliminate inorganic salts such as sulfites, thiosulfates, ammonium, and other organic by-products that raise the COD of the baths and are particularly harmful to the environment.

In addition, because the development process takes place in an aqueous phase, the growth of micro-organisms, in particular in pre-baths, stabilizing baths and wash baths commonly occurs, worsening when the quantities of water consumed are reduced. The growth of micro-organisms such as molds and yeasts, if not controlled, causes the formation of sludge that clog the plant, degrade the processing bath, and so impair the quality of photographic image. Also, the presence of micro-organisms, especially bacteria, causes a biofilm to form on the walls of the processing tanks and on the film drive rollers and wheels, so that the machinery has to be shut down for cleaning.

The use of control agents to prevent or limit bacterial growth in processing baths is common practice. Unfortunately, certain bacterial growth control agents are very sensitive to the presence of sulfites and thiosulfates found in washing water and are broken down before they can fully act. To compensate for this breakdown, excess quantities are used relative to the exact amount required. In this case the water discharged into the environment contains large quantities of bacterial growth control agents, which causes problems in wastewater treatment plants that exploit the action of micro-organisms for effluent treatment.

L. M. Liz-Marzan and A. P. Philipse, in J. Phys. Chem., American Chemical Society, 1995, 99, 15120–15128, describe the synthesis of metal particles in aqueous dispersions of imogolite by reduction of their salts with sodium borohydride. Very stable dispersions of metallic nanoparticles are obtained and can be used for the preparation of catalysts.

The present invention provides a method for preparing a material that minimizes the occurrence and growth of micro-organisms in processing water in order thereby to reduce the quantities of control agents that have to be used.

The present invention provides also a material that rids processing water of pollutant by-products so as to obtain effluents that comply with regulatory requirements.

The present invention provides also a material to rid processing water of pollutant by-products that generate unwanted reactions with bacterial growth control agents, in order thereby to extend the life of said agents.

SUMMARY OF THE INVENTION

The present invention relates to a method for preparing an oxidizing material comprising the step of (i) dispersing in colloidal form a metal or a metal compound in an aqueous solution of an inorganic aluminosilicate polymer, said aluminosilicate being able to form an inorganic gel, and said metal or metal compound being able to cause the oxidation of oxidizable compounds and (or) micro-organisms to be eliminated, and the step of (ii) adding a base to cause said aluminosilicate to gel.

The present invention also concerns a material obtainable by the method described above, as well as its use to oxidize, in the presence of water, oxidizable compounds and (or) micro-organisms to be eliminated.

The invention also concerns a method for treating an aqueous solution liable to contain oxidizable compounds to be eliminated and (or) to harbor micro-organisms, as well as a device for carrying out said method. The method comprises contacting the aqueous solution with said oxidizing material. It is especially efficient for the treatment of photographic baths, in particular wash baths after the fixing step, because it rids such baths of micro-organisms and oxidizable chemical by-products. The "micro-organisms to be eliminated" can be in particular algae, fungi, bacteria and yeasts. The "oxidizable chemicals to be eliminated" can be in particular inorganic or organic by-products considered as pollutants either with regard to aqueous the solution to be treated or in a general way with regard to the environment, for example sulfite and ammonium ions, surfactants, etc.

DETAILED DESCRIPTION OF THE INVENTION

Figure 1:
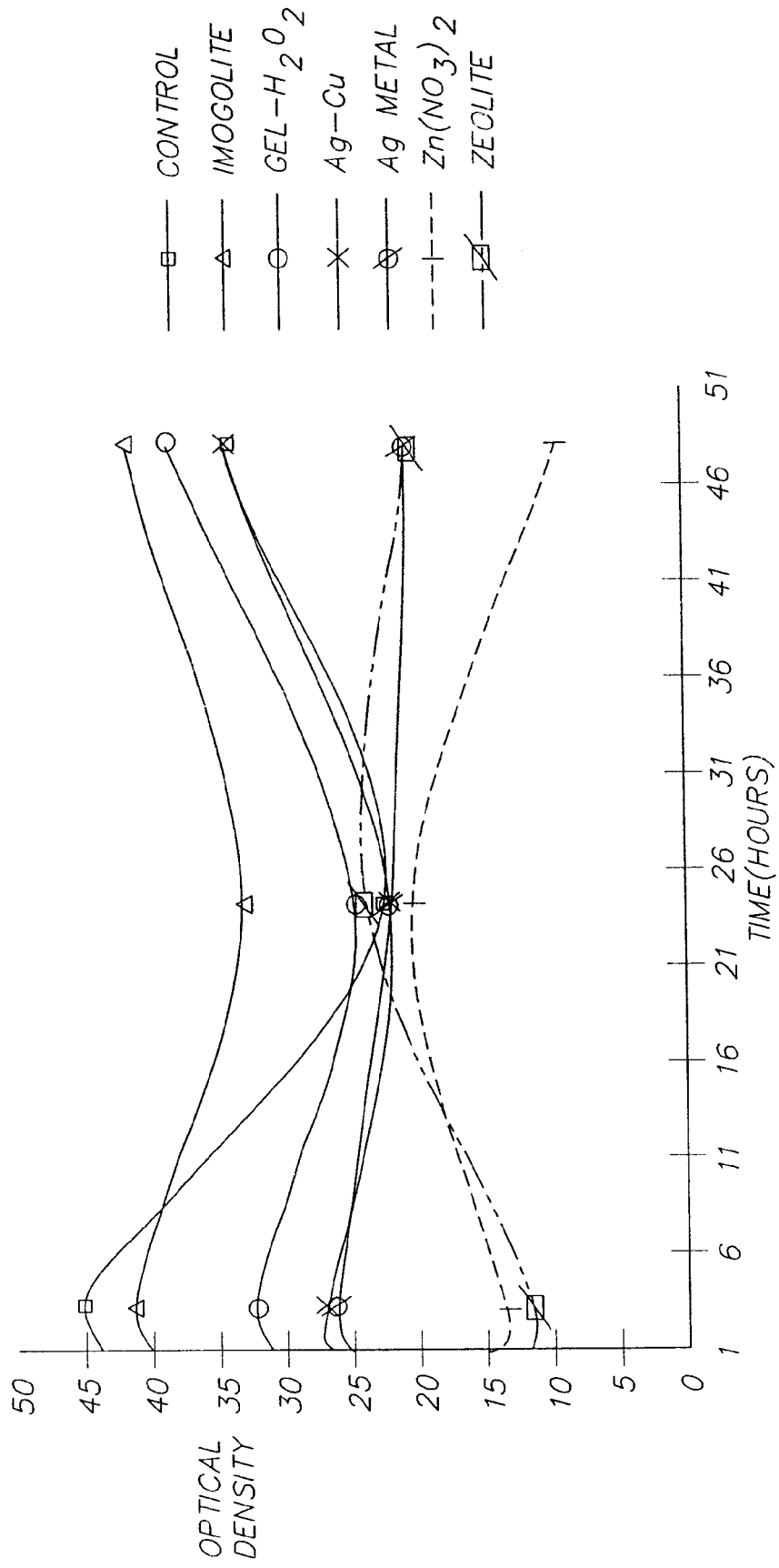
FIG. 1 is a plot of optical density as a function of time for a solution processed with materials according to the invention and comparative materials.

In the method of the invention for preparing an oxidizing material, an aqueous solution of an inorganic aluminosilicate polymer is used that is capable of forming an inorganic gel in certain conditions, for example when the pH of the medium is increased. In a preferred embodiment imogolite is used as aluminosilicate polymer. Imogolite is an aluminosilicate polymer that occurs in the form of fibers, including in solution. An essential characteristic of imogolite is that it forms a gel at a pH of about 8 and above. In this way physical gels are obtained in an aqueous phase. Imogolite fibers comprise active hydroxyl groups on their outer surface. Imogolite occurs naturally in an impure form. It was first described by Wada in J. Soil Sci. 1979, 30(2), 347–355. Imogolite can be synthesized with different degrees of purity by different methods. A method for obtaining a highly pure imogolite gel is described in U.S. Pat. No. 5,888,711.

The metal used in the present invention can be any of the following: silver, zinc, copper, iron, titanium, lead or nickel. When a metal compound is used, the described oxidizing material contains one of the metals listed above. Preferably, monodisperse silver in powder form may be used, in which case most of the particles are of a diameter equal to or smaller than 10 microns, said silver producing a colloid when dispersed in the aqueous solution of imogolite. The silver can be mixed with other metals such as copper. Silver nitrate can also be used as the source of the metal. Zinc can also be used in the form of zinc powder or zinc nitrate. All these metal compounds are commercially available and are distributed, for example, by the Alfa Aesar company.

In the scope of the invention the metals or metal compounds are preferably used in the form of powders that are able to form colloids when they are dispersed in the imogolite. They can also be used in the form of a colloidal solution. However, the pH of the solution must be below the gelling threshold of the imogolite, for example below about 5, so that the addition of the colloidal metal solution does not cause the immediate gelling of the imogolite, which would prevent the metal particles from homogenizing properly in the imogolite solution. The initial metal or metal compound content is preferably in the range of 5 to 10% by weight relative to the [Al+Si] content of the imogolite.

The material according to the invention is obtained by dispersing the metal or metal compound in the aqueous solution of imogolite at ambient temperature, while stirring the solution adequately so as to obtain a homogeneous dispersion of metal particles in colloidal form, and then adding a base to the reaction mixture, for example $NH_4OH$, NaOH or KOH, so as to raise the pH to cause the aluminosilicate to gel.

An imogolite gel is thereby obtained in which metal particles are evenly dispersed, do not agglomerate, and remain dispersed in the imogolite matrix.

The material obtained by the method of the invention displays oxidizing properties. These oxidizing properties are demonstrated in the following way: when the material of the invention is placed at ambient temperature in the presence of cyclohexene dissolved in methanol, the oxidation of cyclohexene into cyclohexanol can be observed by Fourier-transform Raman spectroscopy. The oxidation takes place more readily with heating.

It can be hypothesized that the metal particles dispersed in the imogolite present an appropriate configuration to allow a local micro-electrolysis of water that generates active oxygen, which combines immediately with water to form hydrogen peroxide in situ. According to this hypothesis, the material according to the invention is a gel that allows hydrogen peroxide to be generated in situ, and in which it accumulates. The gel then slowly desorbs the hydrogen peroxide in the aqueous solution to be treated. The hydrogen peroxide, which is unstable, combines immediately with an oxidizable substance and degrades it. This hypothesis is presented for a further understanding of the invention and in no way limits the claims made for the present invention in the event that the mode of operation is proven to be different.

According to one embodiment of the method for preparing the oxidizing material according to the invention, active agents other than the colloidal metal or metal compound are dispersed in the aqueous solution of imogolite, these active agents being chosen so as not to react with the said metal or metal compound. For example, the active agents can be bacterial growth control agents, which are defined as organic compounds displaying pesticidal, algicidal, fungicidal or bactericidal properties. Some bacterial growth control agents are very sensitive to the presence of sodium sulfite or thiosulfate, but only weakly sensitive to oxidation.

A large number of bacterial growth control agents are known. From their general knowledge, those skilled in the art can easily select one or more suitable bacterial growth control agents. However, these agents must not form a covalent bond with the matrix of imogolite gel, because they would then be trapped in the matrix. The bacterial growth control agents that are useful for the invention are, for example, thiazole derivatives such as isothiazolones, azole derivatives such as benzotriazoles, benzimidazoles, or sulfamide-type agents such as sulfanilamide. It is preferable to use a mixture of hydrophilic isothiazolones such as 2-methyl-4-isothiazolin-3-one, and 5-chloro-2-methyl-4-isothiazolin-3-one and hydrophobic isothiazolones such as 2-octyl-4-isothiazolin-3-one. The mixture of hydrophilic and hydrophobic bacterial growth agents is introduced in the oxidizing material of the invention by simple dispersion in the aqueous solution of mogolite before it has gelled.

According to another embodiment of the method for preparing the oxidizing material of the invention, an alkylalkoxysilane of formula $RSiR^1_x(OR^2)_{3-x}$, wherein R is an alkyl group containing an —SH or —S(—$CH_2$)$_n$—S— function with n between 0 and 4, $R^1$ and $R^2$ are independently a methyl or ethyl group and x is 0 or 1, is added to the imogolite and hydrolyzed before the imogolite has been made to gel. A preferred alkylalkoxysilane is 3-mercaptopropyltrimethoxysilane. This process and the material obtained are described in U.S. Pat. No. 6,179,898. It makes it possible to graft onto the surface of the imogolite fibers an organic radical with —SH or —S(—$CH_2$)$_n$—S— function with n between 0 and 4. These sulfur-containing molecules are able to capture the silver present in ionic form in the aqueous solutions to be treated.

These embodiments of the method for preparing the oxidizing material of the invention can be combined in such a way as to obtain a material in which the imogolite matrix comprises grafted sulfur-containing molecules and contains a metal or metal compound dispersed as a colloid, and a bacterial growth control agent.

In the method for treating an aqueous solution according to the invention the oxidizing material described above is placed in contact with the said aqueous solution containing the oxidizable chemicals and (or) the micro-organisms to be eliminated. To be active the oxidizing material of the invention must be permeated by the aqueous solution to be treated, for example an aqueous effluent. The oxidizing material according to the invention can either be placed directly in the solution to be treated or be placed in a container that is permeable to the solution to be treated. It can, for example, be placed in a dialysis bag or in a closed bag made of filter paper or non-woven fabric.

The oxidizing properties of the material of the invention make it possible to eliminate substantially all of the microorganisms that may be present in the effluent, none of which are able to survive in such an oxidizing medium. This makes it possible to reduce the quantity of bacterial growth control agents. The material of the invention can be used in a very broad domain of application, effectively killing, for example, algae, fungi, bacteria and yeasts. The oxidizing material of the invention can be used in any application in which the bacteriological quality of water has to be controlled.

For example, the oxidizing material can be used in the photographic sector, or in the maintenance of industrial cooling water, etc.

The oxidizing material can be advantageously used in a photographic treatment machine conventionally comprising a developing bath, a bleaching bath, a fixing bath and one or more wash baths. The oxidizing material of the invention can be used for any of these baths, preferably for the treatment of a wash bath obtained after the fixing step.

In addition, the oxidizing properties of the material of the invention make it possible to eliminate the oxidizable chemical by-products present in the effluent. Thus certain inorganic salts are readily oxidized, such as sulfites and ammonium ions that occur in large amounts in wash baths. Likewise, certain organic by-products are oxidized, such as surfactants, emulsion thickening agents, etc. As a result, the COD (chemical oxygen demand) of the effluent will be strongly reduced.

Consequently the effluents treated using the material of the invention are rid of by-products that may be controlled by various regulations. In addition, the material of the invention, by affording an in situ oxidation, offers the advantage that hydrogen peroxide solutions do not have to be handled or tanks of oxidizing solution managed.

When the material of the invention also includes bacterial growth control agents dispersed in the imogolite matrix, the method of the invention extends the life of such bacterial growth control agents that are sensitive to sulfites and thiosulfates. The bacterial growth control agents are protected as long as they remain in the imogolite gel matrix. When they diffuse into the effluent to exert their action they are generally destroyed by sulfites and thiosulfates before they can take effect. With the material of the invention the sulfites and thiosulfates present in the effluent are oxidized and broken down before they can destroy the control agents, the concentrations of which in the effluent to be treated therefore remain sufficient. This is particularly useful when the bacterial growth control agent is a curative agent with very high water-solubility designed to massively attack the cells of micro-organisms.

When the material of the invention also contains, on the surface of the imogolite fibers, organic radicals with a sulfur function, ionic silver present in the bath is eliminated in addition to the oxidizable chemicals. Another embodiment of the method of the invention consists in placing the effluent to be treated successively in contact with the oxidizing material of the invention and with a composite material comprising a matrix of imogolite gel in which are dispersed bacterial growth control agents such as those described above and (or) with an inorganic imogolite polymer in fiber form containing at least at the surface of the fibers an organic radical with an —SH or —S(—$CH_2$)$_n$—S— function with n between 0 and 4.

This method offers the same advantages as those described above. In this case the oxidizing material of the invention is placed in contact with the effluent to be treated, or placed in a first dialysis bag, and the composite material for the bacterial growth control or the imogolite comprising grafted sulfur-containing molecules is placed in a second dialysis bag, both bags being placed in a treatment apparatus through which flows the aqueous solution to be treated. The dialysis bags can be arranged so that the treatment by the oxidizing material of the invention is carried out first. The method of the invention can also combine all three treatments, each of the materials, the oxidizing material, the bacterial growth control material and the sulfur-containing material, being placed in separate bags. It is also possible to use the oxidizing material of the invention together with a composite material made up of a matrix of imogolite gel comprising grafted sulfur-containing molecules, and containing a bacterial growth control agent dispersed in the matrix. Such a composite material is described in the Patent application EP-A-937 393.

The following examples illustrate the present invention in detail.

EXAMPLE 1

Preparation of Oxidizing Materials of the Invention
A) Preparation of an Aqueous Solution of Imogolite.

The aluminosilicate of this example was prepared using teachings from U.S. Pat. No. 5,888,711.

To 1,000 ml of de-ionized water were added 16.7 mmoles of tetraethylorthosilicate $Si(OC_2H_5)_4$. The reaction mixture was stirred at ambient temperature for one hour, and then to the solution was added 31.2 moles of $AlCl_3.6H_2O$ dissolved in 1,000 ml of pure water. The mixture was stirred for 20 minutes and the pH was adjusted to 4.5 with 1M NaOH. The solution became cloudy. When the solution became transparent again, 1M NaOH was added until the pH reached 6.8. A white gel was obtained, which was centrifuged for 20 minutes at 2,000 r.p.m. The gel was collected and redissolved in 5 ml of a mixture of 1M HCl and 2M acetic acid. The volume was made up to 2 liters with water. The resulting solution contained 30 mmoles of Al, 16.6 mmoles of Si, 5 mmoles of HCl and 10 mmoles of acetic acid. This solution was stored at 5° C.

This solution was then diluted with de-ionized water to obtain an Al concentration of 10 mmoles/l. The diluted solution was heated for 5 days at 96° C. and then filtered through an ultrafiltration membrane with a separating power of 10,000 daltons (membrane manufactured by AMICON). A clear solution was obtained containing Al and Si in the Al:Si ratio 1.8 and with a [Al+Si] content equal to 3 g/l.

B) Preparation of the Oxidizing Materials

The oxidizing material according to the invention was prepared by dispersing in colloidal form, 20 mg of silver in 200 ml of imogolite prepared according to paragraph A at ambient temperature and at a pH of 4. The silver powders used to make the colloid are referenced −635 mesh and −500 mesh and present a very large number of particles of diameter less than or equal to 10 microns. Such powders are commercialized by the Alfa Aesar company.

To cause the imogolite to gel 10 ml of $NH_4OH$ (15.5M) was then added.

Other materials according to the invention were prepared in a similar way using other metals or metal compounds indicated in Table I (Examples 2–11).

EXAMPLES 2–13

To demonstrate the oxidizing properties of the materials obtained in Example 1, 5 g of one of these materials was placed in contact with 20 ml of cyclohexene dissolved in 80 ml of methanol, and the disappearance of the cyclohexene, readily converted into cyclohexanol by any efficient oxidizing agent, was followed (Examples 2–11). The same experiment was carried out with hydrogen peroxide alone, and with zeolite (Examples 12–13). When no imogolite was present in the test the volume of imogolite was replaced by an equivalent volume of water so as to retain a constant volume.

The oxidation of the cyclohexene was followed by FT (Fourier transform) Raman spectroscopy by measuring the percentage of cyclohexene converted to cyclohexanol after 48 hours. The tests were carried out at ambient temperature.

The results are set out in Table I.

TABLE I

| Examples | | Cyclohexene oxidized after 48 h (%) |
|---|---|---|
| 1 (inv) | Imogolite gel + Ag | 79 |
| 2 (inv) | Imogolite gel + Ag(NO$_3$) | 34 |
| 3 (inv) | Imogolite gel + Ag-Cu | 14 |
| 4 (inv) | Imogolite gel + Cu(NO$_3$)$_2$ | 34 |
| 5 (inv) | Imogolite gel + Zn | 40 |
| 6 (inv) | Imogolite gel + Zn(NO$_3$)$_2$ | 18 |
| 7 (inv) | Imogolite gel + Pb | 35 |
| 8 (inv) | Imogolite gel + Pb(NO$_3$)$_2$ | 37 |
| 9 (inv) | Imogolite gel + Ni | 36 |
| 10 (inv) | Imogolite gel + Fe | 28 |
| 11 (inv) | Imogolite gel + TiO$_2$ | 31 |
| 12 (comp) | Zeolite | 2 |
| 13 (comp) | H$_2$O$_2$ | 3 |

Table I shows that hydrogen peroxide is a weak oxidizing agent, being very difficult to activate. In addition, with zeolite, no oxidation of the cyclohexene was observed.

In contrast, the imogolite gels containing colloidal silver were particularly efficacious oxidizing agents. The imogolite gels containing colloidal zinc, lead or nickel were also oxidizing materials.

EXAMPLES 14–19

An imogolite gel containing Kathon LX®, a mixture of hydrophilic bacterial growth control agents that is completely soluble in water, supplied by Rohm & Haas, was prepared using the following operating procedure.

Kathon LX®: aqueous solution containing 13.7% by weight of isothiazolones of formula:

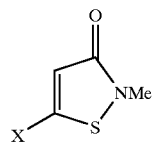

X = Cl, H where the chloroisothiazolone:isothiazolone ratio is 3:1.

Kathon LX® is highly sensitive to the presence of sodium sulfite or thiosulfate. 2 ml of Kathon LX® was mixed with 1 ml of methanol with magnetic stirring. To this mixture was added 100 ml of a 2 g/l solution of imogolite prepared according to Example 1-A. The addition of the mixture of Kathon LX® to the imogolite was carried out with slow mechanical stirring at ambient temperature. Ammonia was then added (0.4 ml). As soon as the gel mass appeared the stirring was stopped.

10 g of the imogolite-Kathon LX® gel thus obtained was placed in a permeable polyester bag.

A sulfite solution was also prepared containing 20% by weight of an equimolar sodium sulfite-thiosulfate mixture.

The polyester bag containing the bacterial growth control agent was placed in 400 ml of the sulfite solution, and then 10 g of an oxidizing material prepared according to Example 1-B was added to the sulfite solution. The mixture was stirred (Examples 14–16).

The same experiment was carried out with the oxidizing material of the invention replaced by an imogolite gel, an imogolite gel plus hydrogen peroxide, and zeolite (Examples 17–19).

The solution was analyzed by UV spectroscopy. The optical density measured against time was characteristic of the quantity of bacterial growth control agent present in the solution. A wavelength of 274 nm is characteristic of Kathon LX®.

The results are set out in Table II below and are illustrated by FIG. 1.

TABLE II

| | Optical density of Kathon LX ® in the presence of sulfites | | | | | |
|---|---|---|---|---|---|---|
| Time (hours) | Control | Ex. 14 Imogolite gel + Ag—Cu (inv) | Ex. 15 Imogolite gel + Ag (inv) | Ex. 16 Imogolite gel + Zn(NO$_3$)$_2$ (inv) | Ex. 17 Imogolite gel (comp) | Ex. 18 Imogolite gel + H$_2$O$_2$ (comp) | Ex. 19 Zeolite (comp) |
| 1 | 17.2 | 15.1 | 22.8 | 26.3 | 8.52 | 25.2 | 20.1 |
| 2 | 13.4 | 32 | 41.1 | 27.4 | 45 | 11.4 | 26 |
| 24 | 20.5 | 24.8 | 33.2 | 22 | 22.6 | 23.8 | 22.1 |
| 48 | 9.6 | 38.5 | 41.9 | 34.8 | 34.6 | 20.8 | 20.6 |

Table II shows that in the control sample (solution of sulfites+Kathon LX®) the optical density and therefore the concentration of Kathon LX® were strongly reduced after 48 hours. Likewise, with zeolite and imogolite gel plus hydrogen peroxide the concentration of Kathon LX® tended to fall with time. In contrast, with the oxidizing materials of the invention there was first a fall in the concentration of Kathon LX®, followed by a marked increase after 48 h. This can be explained by the initial degradation of the Kathon LX® by the sulfites in the sulfite solution, so reducing its concentration. In parallel, the sulfites are oxidized by the oxidizing material of the invention and disappear from the solution. Once the sulfites have been destroyed in this way the Kathon LX® diffusing into the solution is no longer degraded and so its concentration rises. The imogolite gel+Ag of the invention was particularly efficient in extending the life of the Kathon LX® in the sulfite solution.

EXAMPLE 20

T-Mat G® radiographic films supplied by Eastman Kodak were processed in a KODAK X-OMAT® machine, model 5000 RA set for the operating conditions of the KODAK X-OMAT® process described in "Service Bulletin No 30, Health Imaging Products" published by Eastman Kodak Company. These processing lines have a single washing tank placed after the fixing step. The rate of water replenishment in the washing tank was limited to 1 l/min. This washing tank is equipped with an overflow that allows for a constant volume in the tank. The tank was also equipped with an outlet connected by piping to a treatment device according to the invention in which a polyester foam bag was placed, containing 1 kg of the imogolite gel+colloidal silver material made according to Example 1. The treatment device was connected to a pump to send the treated washing water back into the washing bath. The washing water contained, in particular, ammonium ions to be eliminated, and flowed continuously through the treatment tank. By flowing through the oxidizing material of the invention, these ammonium ions were oxidized. The washing water thus treated was then sent back into the processing tank.

To analyze the composition of the treated washing water various samples were taken at the overflow outlet. The washing water sampling procedure was carried out in such a way that the conditions most representative of the average operation of the processing machine were modeled. For this purpose ten T-Mat G® radiographic films of size 35×43 cm were used. Three of them were exposed to light and were completely fogged. At time zero a first unexposed film was introduced into the machine. At time 3 minutes a second unexposed film was introduced. 1 liter of washing water from the overflow of the washing tank was then sampled. At time 6 minutes an exposed film was introduced, and so on until the last film. The unexposed films were thus introduced at times 9, 12, 18, 21 and 27 minutes, and the exposed films at times 15 and 24 minutes.

The sampling of 1 liter of washing water at the overflow outlet was repeated at time 15 minutes during the development of the second exposed film, and again at time 27 minutes, during that of the last unexposed film. The three samples of washing water were pooled, and a 1-liter sample of the resulting mixture was taken.

The 1-liter sample of the treated washing water was analyzed by capillary electrophoresis (CZE, capillary zone electrophoresis) to determine the concentration of $NH_4^+$ and $SO_3^{2-}$ ions.

The experiment was repeated but without treatment of the washing water by the material of the invention.

The results obtained are set out respectively in Tables III and IV below.

TABLE III

| | Treated washing water Concentration in mg/l | |
|---|---|---|
| Species | $t_0$ | $t_0$ + 5 days |
| $NH_4^+$ | 40.30 | 3.90 |
| $SO_3^{2-}$ | 0.00 | 0.00 |

T me $t_0$ corresponds to the first sampling. Before each sampling procedure the bath was seasoned by processing 100 T-Mat G® film plates.

TABLE IV

| | Untreated washing water Concentration in mg/l |
|---|---|
| Species | $t_0$ |
| $NH_4^+$ | 57.90 |
| $SO_3^{2-}$ | 10.00 |

The above results show that the concentration of ammonium ions in the washing water decreased markedly when this washing water was treated with the oxidizing material of the invention. Also, the treated washing water no longer contained any sulfites. After treatment the washing water was compliant with regulations concerning the environment and was fit to be discharged into the sewers. In contrast, the untreated washing water contained high concentrations of ammonium ions owing to the low rate of replenishment of the water in the washing tank.

EXAMPLE 21

The experiment of Example 20 was repeated using, for the KODAK X-OMAT® processing of T-Mat G® films, a KODAK X-OMAT® model 480 RA machine. The water replenishment rate for the washing tank was 3.8 l/min.

The concentration of ammonium ions was measured in 1-liter samples taken as described in Example 20, after several processing runs over several days. The results are set out in Table V below.

TABLE V

| | Treated washing water Concentration in mg/l | | |
|---|---|---|---|
| Species | $t_0$ | $t_0$ + 9 days | $t_0$ + 14 days |
| $NH_4^+$ | 13.20 | 3.90 | 3.30 |

When the washing water was not treated the concentration of $NH_4^+$ ions measured remained greater than or equal to 6.90 mg/l.

The results show that the oxidizing material of the invention reduces the concentration of ammonium ions in washing water significantly and lastingly. This can be explained, according to the hypothesis stated above, by the fact that the hydrogen peroxide generated in situ in the gel, in which it accumulates, is then desorbed slowly into the washing waters that flow continuously through the treatment device.

What is claimed is:

1. A method for preparing an oxidizing material comprising the step of (i) dispersing in colloidal form a metal or metal compound in an aqueous solution of an inorganic aluminosilicate polymer, said aluminosilicate being able to form an inorganic gel, and said metal or metal compound being able to cause the oxidation of oxidizable products and (or) micro-organisms to be eliminated, and the step of (ii) adding a base to cause said aluminosilicate to gel.

2. The method according to claim 1, wherein said metal is selected from among the metals silver, zinc, copper, iron, titanium, lead or nickel, and wherein the metal compound contains at least one of said metals.

3. The method according to claim 2, wherein the metal is silver in powder form of which most of the particles are of diameter less than or equal to 10 microns, and able to form a colloid when dispersed in said aqueous solution of aluminosilicate.

4. The method according to claim 1, wherein said inorganic aluminosilicate polymer is imogolite.

5. The method according to claim 1, further including, before the step (ii), the step of (iii) dispersing a bacterial growth control agent in the aqueous aluminosilicate solution.

6. The method according to claim 1, further including, before the step (ii), the step of (iv) hydrolyzing an alkylalkoxysilane of formula $RSiR^1_x(OR^2)_{3-x}$, wherein R is an alkyl group containing an —SH or —S(—CH$_2$)$_n$—S— function with n between 0 and 4, $R^1$ and $R^2$ are independently a methyl or ethyl group and x is 0 or 1, said aluminosilicate polymer comprising active hydroxyl groups on its surface.

* * * * *